(12) United States Patent
Gratzl et al.

(10) Patent No.: US 11,709,146 B2
(45) Date of Patent: Jul. 25, 2023

(54) MICROFLUIDIC PH-STAT FOR POINT OF CARE (POC) ENZYME DIAGNOSTICS

(71) Applicant: Case Western Reserve University, Cleveland, OH (US)

(72) Inventors: Miklos Gratzl, Cleveland, OH (US); Tamas Cseefalvi, Cleveland, OH (US); Christian Zorman, Cleveland, OH (US); John W. Stanton, Cleveland, OH (US); Zhehao Zhang, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 756 days.

(21) Appl. No.: 16/701,682

(22) Filed: Dec. 3, 2019

(65) Prior Publication Data
US 2020/0173951 A1    Jun. 4, 2020

Related U.S. Application Data

(60) Provisional application No. 62/774,379, filed on Dec. 3, 2018.

(51) Int. Cl.
| | |
|---|---|
| *G01N 27/30* | (2006.01) |
| *G01N 33/573* | (2006.01) |
| *G01N 33/84* | (2006.01) |
| *G01N 33/543* | (2006.01) |
| *C12Q 1/25* | (2006.01) |

(52) U.S. Cl.
CPC ............. *G01N 27/302* (2013.01); *C12Q 1/25* (2013.01); *G01N 33/5438* (2013.01); *G01N 33/573* (2013.01); *G01N 33/84* (2013.01)

(58) Field of Classification Search
CPC .... C12Q 1/25; G01N 27/302; G01N 33/5438; G01N 33/573; G01N 33/84
See application file for complete search history.

(56) References Cited

PUBLICATIONS

Kao, "Point-of-care body fluid diagnostics in microliter samples," Dissertation, Case Western Reserve University, May 2009.*
Araz et al., "Microfluidic Multiplexing in Bioanalyses," J. Lab. Automation, 2013, vol. 18, issue 5, pp. 350-366.*
Kao, Linus T-H., Hung-Yi Hsu, and Miklós Gratzl. "Reagentless pH-stat for microliter fluid specimens." Analytical chemistry 80.11 (2008): 4065-4069.
Kao, Linus T-H., and Miklos Gratzl. "Serum cholinesterase assay using a reagent-free micro pH-stat." Analytical Biochemistry 389.2 (2009): 93-96.

* cited by examiner

*Primary Examiner* — Galina M. Yakovleva
(74) *Attorney, Agent, or Firm* — Tarolli, Sundheim, Covell & Tummino LLP

(57) ABSTRACT

A microfluidic pH-stat with a specially-is designed slide and portable device can be used for point-of-care enzyme diagnostics. The slide includes a microchamber and a substrate for the enzyme being tested. The substrate is homogenized with the sample in the microchamber to form a test volume. The microchamber includes a working microelectrode that injects current to split water in the test volume to generate hydrogen ions and/or hydroxide ions and a micro-pH-electrode to measure a pH of the test volume; the slide also includes a reference microelectrode. The device includes a processor to adjust the injected current based on the pH of the test volume and determine an activity of the enzyme based on an amount the injected current is adjusted.

6 Claims, 4 Drawing Sheets

MICROFLUIDIC PH-STAT FOR POINT OF CARE (POC) ENZYME DIAGNOSTICS

RELATED APPLICATION

This application claims priority to U.S. Provisional Application Ser. No. 62/774,379, filed Dec. 3, 2018, entitled "MICROFLUIDIC PH-STAT SLIDE FOR ENZYME DIAGNOSTICS". The entirety of this application is hereby incorporated by reference for all purposes.

TECHNICAL FIELD

The present disclosure relates generally to point-of-care (POC) diagnostics and, more specifically, to systems and methods that provide a microfluidic pH-stat using a specially-designed slide and portable device for POC enzyme diagnostics.

BACKGROUND

Enzymes are frequently used as biomarkers of a diverse set of diseases. Accordingly, the presence and severity of many health conditions can be assessed using enzyme activity tests (also referred to as "enzyme diagnostics". Traditional enzyme diagnostics were performed in centralized laboratories, which added time and expense to the diagnostic process. Even as testing has moved into the point-of-care (POC), enzyme diagnostics remain enzyme-specific, expensive, not absolute, and not portable, and require long turnaround times.

SUMMARY

The present disclosure generally relates to a microfluidic pH-stat, using a specially-designed slide and portable device, specifically designed for point-of-care (POC) enzyme diagnostics to be portable and inexpensive. The microfluidic pH-stat is not enzyme-specific and, instead, can provide accurate absolute information related to enzyme activities of a plurality of enzymes over a range of several orders of magnitude without the need for calibration, reagents, or significant labor.

In an aspect, the present disclosure can include a system that can perform POC enzyme diagnostics using a specifically designed microfluidic pH-stat with a specially-designed slide and portable device. The slide includes a slide comprising a substrate for an enzyme and is configured to hold a microvolume of a sample including the enzyme (e.g., a small droplet with a volume less than 20 µL, such as a volume from 1-5 µL) by wicking the sample within a microchamber. The substrate is homogenized with the sample to form a test volume within the microchamber. The device is configured to receive the slide, and comprises a working electrode, the pH electrode, and the reference electrode. The microchamber comprises contacts for the working microelectrode configured to receive an injected current that splits water in the test volume to generate hydrogen ions and/or hydroxide ions based on a reaction between the enzyme and the substrate; and a contact for a micro-pH-electrode configured to measure a pH of the test volume. The slide comprises a contact and a reference microelectrode (which may be remote from the microchamber). The device also includes a main unit comprising a processor that is configured to adjust the injected current based on the pH of the test volume to ensure that the pH of the test volume remains constant and determine an activity of the enzyme in the test volume based on an amount the injected current is adjusted to ensure that the pH of the test volume remains constant.

In another aspect, the preset disclosure can include a device (e.g., a slide, which can be disposable) of a specifically designed microfluidic pH-stat to be used in POC enzyme diagnostics. The device is includes a microchamber configured to wick the test volume (e.g., a small droplet with a volume less than 20 µL, such as a volume from 1-5 µL) into the microchamber, which includes a substrate for the enzyme being tested and contacts for a working microelectrode, a pH microelectrode, and/or a reference microelectrode (this contact may be remote from the channel). The working electrode is configured to receive an injected current that splits water in the test volume to generate hydrogen ions and/or hydroxide ions based on a reaction between the enzyme and the substrate; the micro-pH-electrode can be configured to measure a pH of the test volume; and a reference microelectrode. The injected current can be adjusted based on the pH of the test volume to ensure that the pH of the test volume remains constant and determine an activity of the enzyme in the test volume based on an amount the injected current is adjusted to ensure that the pH of the test volume remains constant. For example, the injected current and the pH-stat can be provided by a testing device including a processor that includes the working electrode, the reference electrode, and the reference electrode. The benefit of the microchamber is the ability for the test volume and/or the H+ and/or OH– molecules to diffuse into the test volume without requiring external stirring.

In another aspect, the present disclosure can include a method for POC enzyme diagnostics using a specifically designed microfluidic pH-stat with a specially-designed slide and portable device. A microvolume of a sample (potentially including a concentration of an enzyme) can be wicked into a microchamber of a slide that includes a substrate for the enzyme. The substrate can be allowed to diffuse within the microvolume of the sample to form a test sample within a microchamber of the slide. The slide can be inserted into a device, which acts as a pH stat. An activity of the enzyme in the test sample can be determined based on an amount an injected current is adjusted to ensure that the pH of the test sample remains constant.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
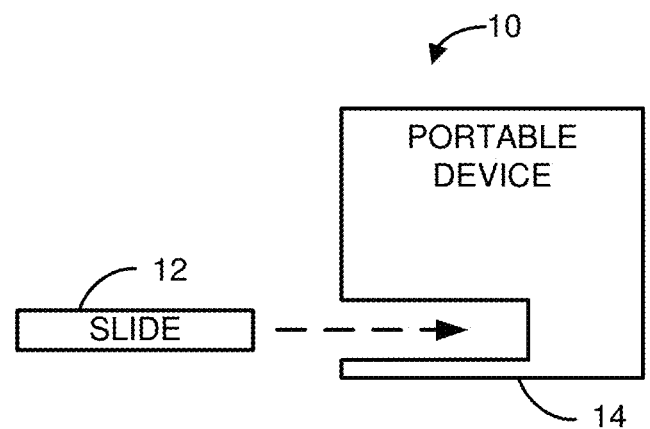
FIG. 1 is a diagram showing a system that facilitates point of care (POC) enzyme diagnostics in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "point-of-care (POC) testing" can refer to medical diagnostic testing at the time and place of patient care. POC testing can occur in real time without requiring hours or days of traditional laboratory testing. A type of testing can be accomplished at the POC can be enzyme diagnostics.

As used herein, the term "enzyme diagnostics" (also referred to as "enzyme activity tests") can refer to a measurement of the activity of a specific enzyme in a sample. The enzyme diagnostics can be used for many applications, for example: to test for the presence and severity of many diseases and conditions, including anemia (based on lactate dehydrogenase activity), pancreatitis (based on amylase or lipase activity), and defects in the glucose-6-phosphate-dehygenase (G6PD) enzyme; to optimize treatment for a disease, such as childhood acute lymphoblastic leukemia (ALL) (based on L-asparaginase levels); to test for diseases affecting public health, such as malaria; to detect fermentation, such as in the food industry; for environmental and/or pharmaceutical applications, such as in soil analysis, production of medicines or precursors and intermediates.

As used herein, the term "enzyme" can refer to a substance that acts as a catalyst to bring about a specific chemical reaction.

As used herein, the term "substrate" can refer to a material upon which an enzyme acts. For example, the enzyme can catalyze a chemical reaction that involves the substrate.

As used herein, the term "pH-stat" can refer to a device configured to maintain a pH of a sample at a constant level by managing acid-base concentration.

As used herein, the term "microelectrode" can refer to an electrode with at least one geometric feature sized less than 500 microns or less.

As used herein, the term "sample" can refer to a small quantity used to represent a whole. For example, the sample can be a small volume of bodily fluid (e.g., whole blood, serum, plasma, interstitial fluid, urine, cerebral spinal fluid, etc.) taken from a patient. In some instances, a portion of the sample that is analyzed can be very small, like less than 20 µL.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

Enzyme diagnostics (also referred to as enzyme activity tests) are used to test and confirm the presence and severity of many diseases and conditions. Traditional enzyme diagnostics have been enzyme-specific, expensive, not absolute, and not portable. Described herein is a microfluidic pH-stat, including a specially-designed slide and portable device, that can be used for quantitative/absolute, portable, low cost point-of-care (POC) enzyme diagnostics for a plurality of different enzymes. The specially-designed slide is disposable and loaded with a substrate specific to an enzyme of interest. The microfluidic pH-stat can be reused for different enzymes with different slides having different substrates specific to different enzymes.

The microfluidic pH-stat requires only a very small sample volume that may include a certain enzyme and performs fully electrochemical pH-stating on the very small volume. Notably, the microfluidic pH stat works for any enzyme of interest that influences the pH of the sample solution by producing or consuming $H^+$ or $OH^-$ or consuming either of them during the associated catalytic reaction using the specially-designed, disposable slide with an appropriate substrate and a single portable device. The disposable slide is designed such that the small sample volume and the substrate can be homogenized via spontaneous diffusion (or other ways of homogenizing without stirring). The device includes a microchannel that wicks in the sample (including the homogenized enzyme and substrate) and contains three microelectrodes: a working electrode, a pH electrode, and a reference electrode. The working electrode uses electrolytic water splitting to inject (or generate) $OH^-$ or $H^+$ ions into the sample (including the homogenized enzyme and substrate) at a rate that counterbalances the pH-shift induced by the catalytic reaction such that the rate is exactly equal to the rate of the catalytic reaction. The pH electrode measures the pH such that the pH shift to be compensated for is determined. At stationary "stated" pH, the injected current is equivalent to enzyme activity via Faraday's number, making the pH stat absolute (calibration free).

III. Systems

One aspect of the present disclosure can include a system 10 (FIG. 1) that that facilitates point of care (POC) enzyme diagnostics (also referred to as enzyme activity tests). Enzyme activities, either two low or too high, are indicators of the presence of many diseases and conditions, including anemia (based on lactate dehydrogenase activity), pancreatitis (based on amylase or lipase activity), and defects in the glucose-6-phosphate-dehygenase (G6PD) enzyme; to optimize treatment for a disease, such as childhood acute lymphoblastic leukemia (ALL) (based on L-asparaginase levels); to test for diseases affecting public health, such as malaria; to detect fermentation, such as in the food industry; for environmental and/or pharmaceutical applications, such as in soil analysis, production of medicines or precursors and intermediates. Most enzyme diagnostics are currently performed in central laboratories of hospitals; very few enzyme diagnostics are performed at the POC, and those that are performed at the POC are enzyme-specific, expensive, not absolute, and/or not portable. The system 10 provides a microfluidic pH-stat, including a specially-designed slide 12 and portable device 14, that can be used for quantitative/absolute, portable, low cost POC enzyme diagnostics for a plurality of different enzymes.

As an example, the system 10 can be capable of measuring about 50% of all clinically significant enzymes using the same portable device 14 and different disposable enzyme-specific microfluidic slides. In fact, any enzyme that generates an acid or base shift in at least one catalytic conversion step can be identified according to the enzyme diagnostic performed by the system 10. For example, the enzymes may produce $H^+$ ions or $OH^-$ ions as reaction products from a catalyzed reaction with a substrate, thereby shifting the pH of a sample. The system 10 can inject either $OH^-$ ions or $H^+$ ions into the sample at the same rate the reaction products are produced, such that the rate of injection of either $OH^-$ ions or $H^+$ ions that stabilize the pH in the solution (by electrolytic water splitting) is equal to the rate of the enzyme reaction via Faraday's number (also referred to as Faraday's constant—representing the amount of electric charge carried by one mole, or Avogadro's number, of electrons, represented by F and expressed in coulombs per mole). Therefore, the current that is required to stabilize (or "stat") the pH of the sample reflects enzyme activity such that calibration is not necessary.

Figure 2:
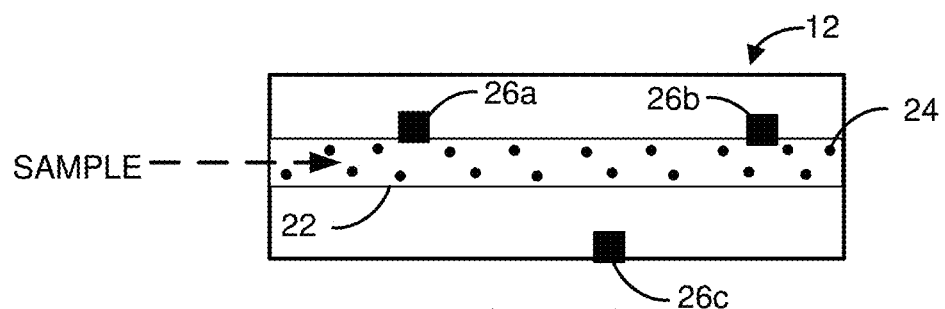
FIG. 2 is a diagram showing a top view of a slide that can be used by the system in FIG. 1.
Figure 3:
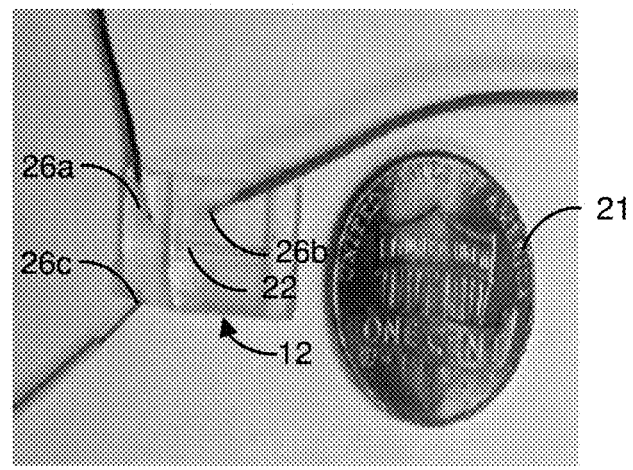
FIG. 3 is a photograph of an example slide that can be used by the system in FIG. 1.
Figure 4:
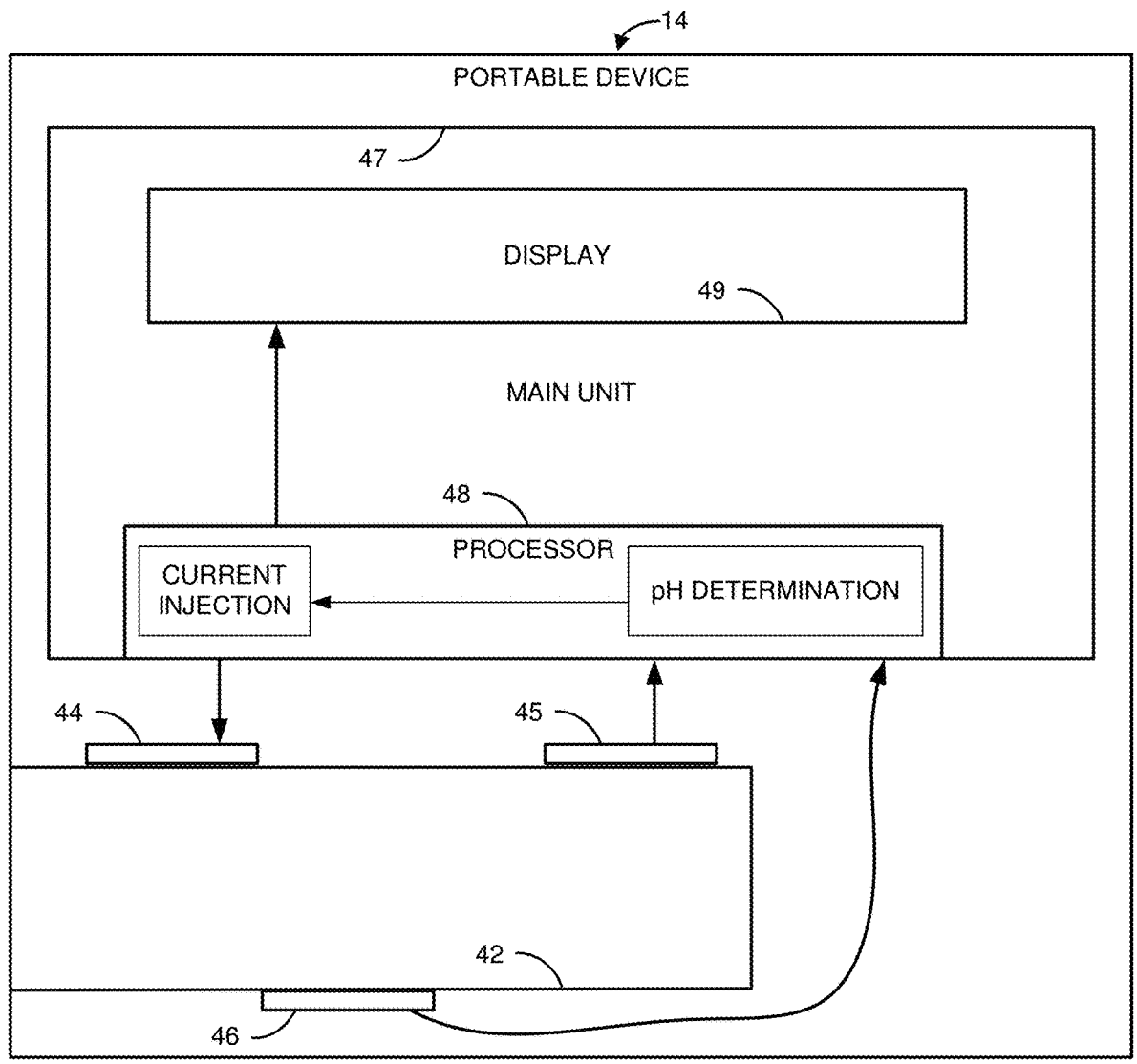
FIG. 4 is a diagram of portable device that can be used by the system in FIG. 1.

The system 10 can include a slide 12, which is shown in more detail in FIGS. 2 and 3, and a portable device 14, which is shown in more detail in FIG. 4. It its simplest form, the slide can receive a volume of a sample (which may or may not include an enzyme of interest). The slide 12 can include a substrate specific to the enzyme and be specially chosen for the enzyme of interest. The sample within the slide may be experiencing a catalytic reaction of the enzyme and a substrate. The portable device 14 can then determine an enzyme activity within the portion of the volume. Notably, the slide 12 requires only a very small volume of the sample, and the slide 12 facilitates diffusion (or other passive mixing without physical stirring) of the substrate, $H^+$ and/or $OH^-$ through the sample (or a test sample after the substrate is mixed with the enzyme).

FIG. 2 shows a top view of an example slide 12 that is disposable and specific to a certain enzyme of interest. FIG. 3 is a photograph of an example slide 12, emphasizing the small size of the slide 12—smaller than a U.S. penny 21. The slide 12 has a microchannel 22 that is loaded with a substrate 24 specific for the certain enzyme of interest and has at least three electrode contacts 26a, 26b, and 26c.

The microchannel 22 requires only a very small sample volume (e.g., 10 μL or less) that may contain a certain enzyme. The sample volume can be wicked into the microchannel 22. The slide 12 can include a concentration of a substrate 24 within the microchannel 22. The microchannel 22 can extend across any portion of the slide 12—as shown in FIG. 2, the microchannel 22 can extend across the entire width of slide 12, while, as shown in FIG. 3, the microchannel 22 can extend for a portion of the width of the slide 12 less than the entirety. The substrate 24 can be immobilized on the slide 12—e.g., within the microchannel 22. When the sample volume is wicked into the microchannel 22, the substrate 24 becomes able to mix with the sample volume via diffusional mixing (or other passive mixing that is not stirring). As an example, the sample volume can be 2 μL, where the slide 12 comprises a 10 mm long microchannel 22 with a 0.32×0.64 mm cross section and longitudinal microelectrodes, the short distances within a cross section making it possible to achieve homogeneity without mechanical stirring.

The at least three electrode contacts 26a, 26b, and 26c can be microelectrodes, including a working microelectrode contact 26a, a micro-pH electrode contact 26b, and a reference microelectrode contact 26c. At least one of the working microelectrode contact 26a, the micro-pH electrode contact 26b, and the reference microelectrode contact 26c can be located within the channel. For example, any electrode contacts located within the microchannel can be deposited by microprinting. As shown in FIG. 2, the working microelectrode contact 26a and the micro-pH electrode contact 26b are located within the microchannel 22, while the reference microelectrode contact 26c is located remote from the channel. As an example, the working microelectrode contact 26a comprises a metal, the micro-pH-electrode contact 26b comprises at least one of iridium oxide or palladium (either may be in the form of dots or microbeads or nanobeads dispersed within the sample and/or printed on the microchannel 22 walls), and the reference microelectrode contact 26c comprises at least one of silver and silver chloride.

The slide 12 can be inserted into the portable device 14, as shown in FIG. 4. The portable device 14 can include an insertion area 42 and a main unit 47. The insertion area 44 can be shaped to receive the slide 12 and includes at least electrodes 44, 45, and 46 that can interface with the at least three electrode contacts 26a, 26b, and 26c to establish electrical connections. The electrodes 44, 45, and 46 can be located in known pre-designed positions within the main unit and the slide 12 can be designed mindful of the locations of the electrodes 44, 45, and 46 and the shape of the insertion area. Electrode 44 can be a current insertion electrode, electrode 45 can be a pH electrode, while electrode 46 can be a reference electrode. The electrical connections can be established when the slide 12 is inserted. The portable device 14 can be used for different slides with different substrates testing for different enzymes because the portable device 14 has nothing specific to any enzyme—the slide 12 is the only component specific to an enzyme.

The electrodes 44, 45, and 46 can be in communication with a processor 48 within the main unit 47. The processor receives a signal from the pH electrode 45, determines the pH and/or a change in pH of the sample, determines a change in pH and a current necessary to generate an amount of $H^+$ or $OH^-$ required to make the pH of the sample static or neutral, and injects the current into the sample. The current injection is generally based on the principle that each individual enzyme conversion step generates a known amount of $H^+$ or $OH^-$, which can be exactly counterbalanced by adding the same number of $OH^-$ or $H^+$ to the sample by electrolytic water splitting. The rate that the $OH^-$ or $H^+$ is added to the sample is equivalent to a reaction rate of the reaction catalyzed by the enzyme. The current injection can be constant and/or pulsed. Determining the rate of extraneous base or acid addition that keeps the pH constant readily translates into the activity of the enzyme in question in the solution. For example, the change or adjustment in the current (addition or reduction) can be directly related to the enzyme activity. The processor 48 can send a value related to the enzyme activity (e.g., the total amount of current injected and/or the enzyme activity and/or another property related to the enzyme activity) to a display 49 (e.g., a graphical user interface (GUI)) for display to a user (e.g., a physician, a nurse, a testing professional, or the like) to make a diagnosis.

IV. Methods

Another aspect of the present disclosure can include methods 50 and 60 (FIGS. 5 and 6) using a microfluidic pH-stat for enzyme diagnostics. The methods 50 and 60 can be executed using the system 10 shown in FIG. 1, with components shown in FIGS. 2-4, and described above.

The methods 50 and 60 are illustrated as process flow diagrams with flowchart illustrations. For purposes of simplicity, the methods 50 and 60 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 50 and 60.

Figure 5:
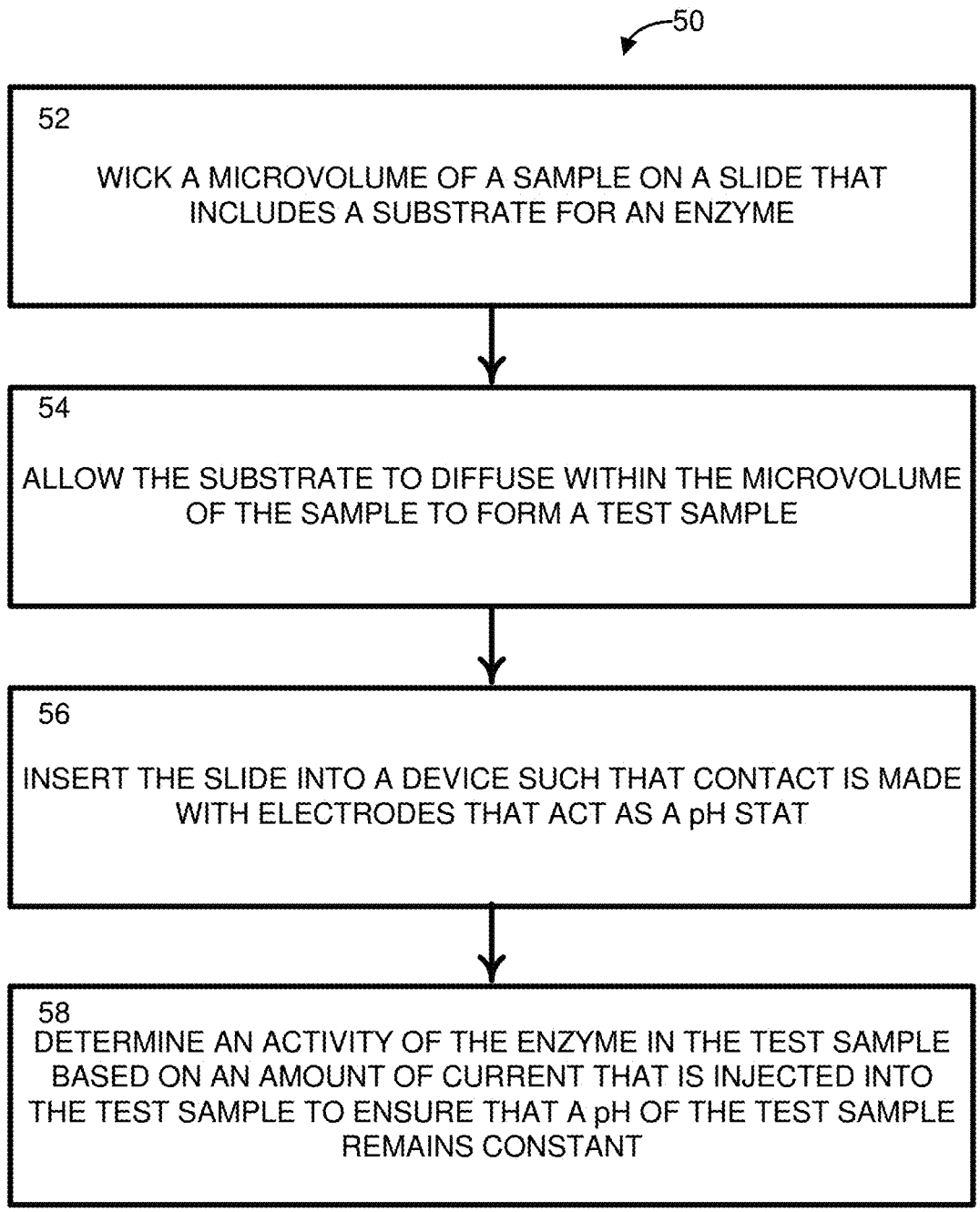
FIGS. 5 and 6 are process flow diagrams illustrating a method for using a microfluidic pH-stat for enzyme diagnostics according to another aspect of the present disclosure.

Referring now to FIG. 5, illustrated is a method 50 for using a microfluidic pH-stat for enzyme diagnostics. The enzyme diagnostics can be used for many applications, for example: to test for the presence and severity of many diseases and conditions, including anemia (based on lactate dehydrogenase activity), pancreatitis (based on amylase or lipase activity), and defects in the glucose-6-phosphate-dehygenase (G6PD) enzyme; to optimize treatment for a disease, such as childhood acute lymphoblastic leukemia (ALL) (based on L-asparaginase levels); to test for diseases affecting public health, such as malaria; to detect fermentation, such as in the food industry; for environmental and/or pharmaceutical applications, such as in soil analysis, production of medicines or precursors and intermediates. The microfluidic pH-stat can include a slide 12 of FIG. 1, shown in FIGS. 2-3, and a portable device 14 of FIG. 1, shown in FIG. 4.

At Step 52, a microvolume of a sample can be wicked into a disposable slide that includes a substrate for an enzyme (the substrate can engage in a known reaction that is catalyzed by the enzyme to produce or consume $H^+$ or $OH^-$). In some instances, the microvolume of the sample can be less than 20 µL. In other instances, the microvolume of the sample can be less than 10 µL. In still other instances, the microvolume of the sample can be less than 5 µL. In some other instances, the microvolume of the sample can be less than 3 µL. The sample may include a concentration of an enzyme. The substrate (and, accordingly, the slide) can be selected based on the enzyme that may exist in the sample. In some instances, the substrate can be immobilized on the slide before the sample is placed on the slide. At Step 54, the substrate can be allowed to diffuse within the microvolume of the sample to form a test sample. The presence of the sample can dislodge the immobilized substrate such that the substrate can diffuse within the sample.

At Step 56, the slide can be inserted into a device such that contact is made with electrodes that can act as a pH stat. In some instances, the electrodes can be three electrodes include a working microelectrode to inject a current that splits water in the test volume to generate hydrogen ions and/or hydroxide ions based on a reaction between the enzyme and the substrate; a micro-pH-electrode configured to measure the pH of the test volume; and a reference electrode. At least one of the working microelectrode, the micro-pH-electrode, and the reference microelectrode is printed onto a wall of the microchamber. In some instances, at least two of the working microelectrode, the micro-pH-electrode, and the reference microelectrode is printed onto a wall of the microchamber. In other instances, all three of working microelectrode, the micro-pH-electrode, and the reference microelectrode is printed onto a wall of the microchamber are printed onto a wall of the microchamber. As an example, the working microelectrode comprises a metal, the micro-pH-electrode comprises at least one of iridium oxide or palladium (either may be in the form of dots or microbeads or nanobeads), and the reference microelectrode comprises at least one of silver and silver chloride. At Step 58, an activity of the enzyme in the test sample can be determined based on an amount of current that is injected into the test sample to ensure that a pH of the test sample remains constant. For example, the change or adjustment in the current (addition or reduction) can be directly related to the enzyme activity.

Figure 6:
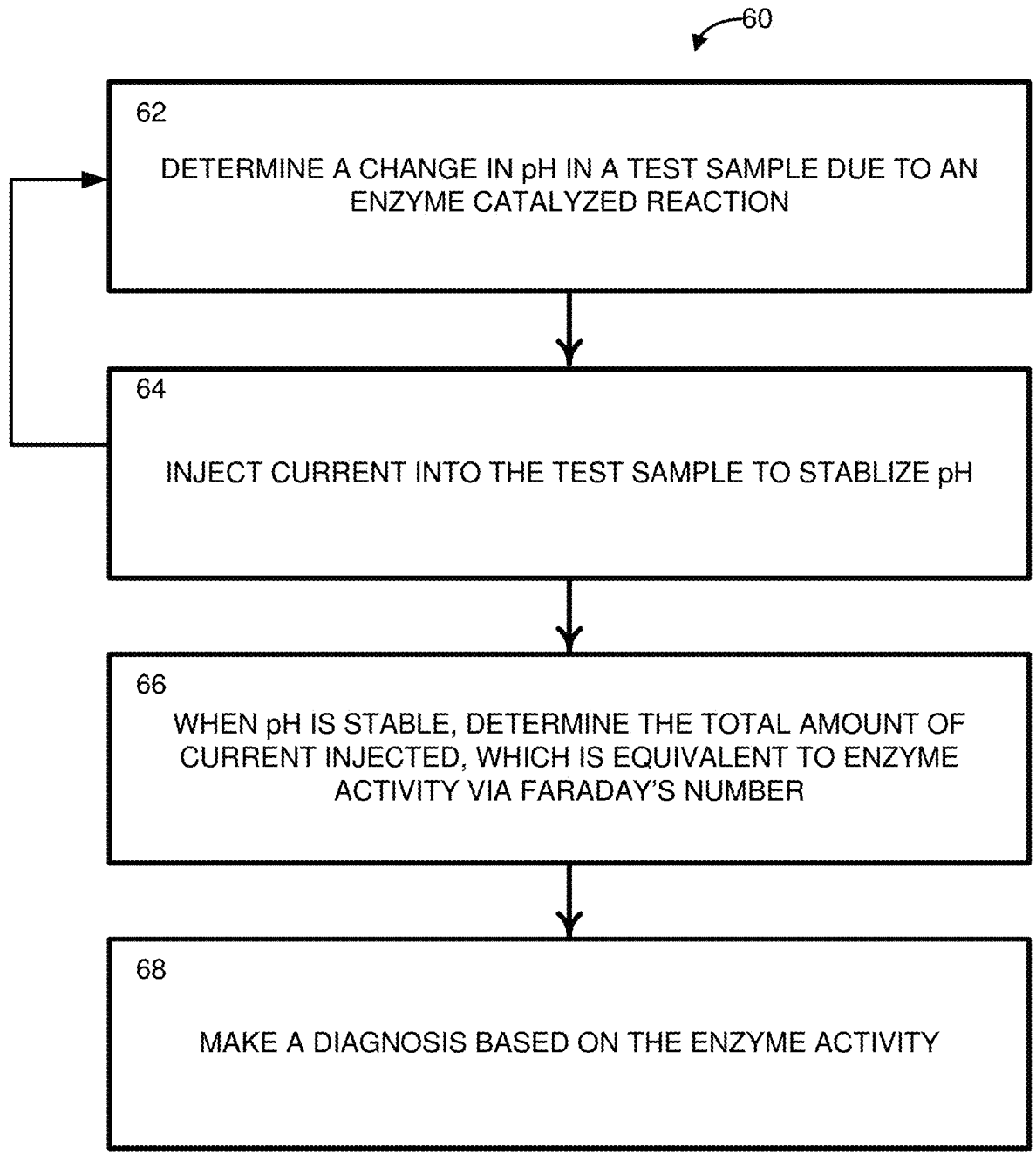

Referring now to FIG. 6, illustrated is another method 60 for determining enzyme activity, which is used to enzyme diagnostics by a microfluidic pH-stat. The method 60 shows a specific example of Step 58 of FIG. 5. This method 60 can occur within the portable device 14 of FIG. 1 that is shown in greater detail in FIG. 4.

At Step 62, a change in a pH in a test sample due to an enzyme catalyzed reaction with the substrate can be determined. This determination can be made by a processor according to an input from a pH sensor and a previous pH value. Based on the pH change, the processor can determine how much current needs to be injected into the test sample to neutralize the test sample. At Step 64, a current can be injected to neutralize/stabilize the pH in the test sample. The current can be injected by a working electrode based on the determination by the processor. Steps 62 and 64 can be repeated until the pH in the test sample has been neutralized/stabilized.

At Step 66, when the pH is stable (or neural), the total amount of current injected can be determined. The total amount of current injected is equivalent to enzyme activity via Faraday's number. In other words, the current can be converted into moles per time via Faraday's number (also referred to as Faraday's constant—representing the amount of electric charge carried by one mole, or Avogadro's number, of electrons, represented by F and expressed in coulombs per mole). In some instances, the total amount of current injected and/or the enzyme activity and/or another property related to the enzyme activity can be displayed on a graphical user interface (GUI) of the portable device. At Step 68, a diagnosis can be made based on the total amount of current injected and/or the enzyme activity and/or another property related to the enzyme activity.

From the above description, those skilled in the art will perceive improvements, changes and modifications. Such improvements, changes and modifications are within the skill of one in the art and are intended to be covered by the appended claims.

The following is claimed:

1. A system comprising:
   a disposable slide comprising a microchannel, wherein the microchannel comprises a substrate for an enzyme, wherein the slide is configured to wick a volume of a sample including the enzyme into the microchannel, wherein the substrate is homogenized with the sample in the microchannel to form a test volume, wherein the slide further comprises a working microelectrode contact, a micro-pH electrode contact, and a reference microelectrode contact, the working microelectrode contact and the micro-pH electrode contact are located on at least one wall of the microchannel and the reference microelectrode contact is located on a different portion of the slide; and
   a portable device for point-of-care (POC) enzyme diagnostics, comprising:

an insertion area shaped to receive the slide, the insertion area comprising:
- a working microelectrode configured to electrically interface with the working microelectrode contact of the received slide and to inject a current into the test volume, via the working microelectrode contact, that splits water in the test volume to generate hydrogen ions and/or hydroxide ions based on a reaction between the enzyme and the substrate;
- a micro-pH-electrode configured to electrically interface with the micro-pH microelectrode contact of the received slide and to measure a pH of the test volume; and
- a reference microelectrode configured to electrically interface with the reference microelectrode contact of the received slide; and a main unit comprising a processor configured to adjust the injected current based on the pH of the test volume to ensure that the pH of the test volume remains constant and determine an activity of the enzyme in the test volume based on an amount the injected current is adjusted to ensure that the pH of the test volume remains constant.

2. The system of claim 1, wherein the main unit further comprises a graphical user interface (GUI) to display the activity of the enzyme in the test sample.

3. The system of claim 1, wherein the activity of the enzyme in the test sample is determined by converting the current into moles per time via Faraday's number.

4. The system of claim 1, wherein of the working microelectrode contact and the micro-pH-electrode contact are printed onto the at least one wall of the microchannel.

5. The system of claim 1, wherein the substrate is immobilized on the slide before the sample is received.

6. The system of claim 5, wherein the substrate is able to disperse within the volume of the sample to become homogenized with the sample via diffusional mixing to form the test volume.

* * * * *